United States Patent [19]

Smith et al.

[11] Patent Number: 5,908,830

[45] Date of Patent: Jun. 1, 1999

[54] COMBINATION THERAPY FOR THE TREATMENT OF DIABETES AND OBESITY

[75] Inventors: Roy G. Smith, Westfield; Margaret A. Cascieri, East Windsor; Euan MacIntyre, Scotch Plains; Douglas J. MacNeil, Westfield; John G. Menke, Morganville, all of N.J.

[73] Assignee: Merck & Co., Inc., Rahway, N.J.

[21] Appl. No.: 08/961,749

[22] Filed: Oct. 30, 1997

Related U.S. Application Data

[60] Provisional application No. 60/029,233, Oct. 31, 1996.

[51] Int. Cl.$^6$ .......................... A61K 38/00; A61K 31/24; C07K 5/00; C07K 16/00
[52] U.S. Cl. .......................... 514/12; 530/324; 530/350; 514/312; 424/309
[58] Field of Search .................. 530/350, 324; 514/12

[56] References Cited

U.S. PATENT DOCUMENTS

| | | | |
|---|---|---|---|
| 4,396,627 | 8/1983 | Ainsworth et al. | 424/309 |
| 4,478,849 | 10/1984 | Ainsworth et al. | 424/285 |
| 5,451,677 | 9/1995 | Fisher et al. | 546/138 |
| 5,516,653 | 5/1996 | Bald et al. | 435/69.1 |
| 5,545,549 | 8/1996 | Gerald et al. | 435/240.2 |
| 5,552,524 | 9/1996 | Basinski | 530/324 |
| 5,554,621 | 9/1996 | Poindexter et al. | 514/278 |
| 5,561,142 | 10/1996 | Fisher et al. | 546/153 |
| 5,602,024 | 2/1997 | Gerald et al. | 435/240.2 |
| 5,635,503 | 6/1997 | Poindexter et al. | 514/218 |

FOREIGN PATENT DOCUMENTS

| | | |
|---|---|---|
| WO 93/09227 | 5/1993 | WIPO . |
| WO 95/17906 | 7/1995 | WIPO . |
| WO 95/21245 | 8/1995 | WIPO . |
| WO 95/29159 | 11/1995 | WIPO . |
| WO 96/16542 | 6/1996 | WIPO . |

OTHER PUBLICATIONS

De Vos et al, J. Biol Chem, vol. 270. No. 27, Jul. 7, pp. 15958–15961.

*Primary Examiner*—Cecilia J. Tsang
*Assistant Examiner*—S. G. Marshall
*Attorney, Agent, or Firm*—Kenneth R. Walton; Melvin Winokur

[57] ABSTRACT

The combination of a metabolic rate modifying agent (e.g., a $\beta_3$ adrenergic receptor agonist) and a feeding behavior modifying agent (e.g., a NPY5 antagonist) is useful in the treatment of obesity and diabetes, either as compounds, pharmaceutically acceptable salts, pharmaceutical composition ingredients. Methods of treating obesity and diabetes are also described.

20 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:1:

CAGTGAGCCC CAAGAAGAGG          20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

TCCAGGTCAT TGGCTATCTG          20

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:3:

ATTCCTGGGC TTCAGGGGAT TCTGAGTTTC          30

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:4:

GCGTGTACCC ACGGAGGAAC          20

(2) INFORMATION FOR SEQ ID NO:5:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (xi) SEQUENCE DESCRIPTION: SEQ ID NO:5:

```
AAGAATTCAT GTTGCTGGAG ACCCCTGTGT C                                             31

(2) INFORMATION FOR SEQ ID NO:6:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:6:

AAGGATCCTC AGCATTCAGG GCTAACATC                                                29

(2) INFORMATION FOR SEQ ID NO:7:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:7:

Val Pro Ile Gln Lys Val Gln Asp Asp Thr Lys Thr Leu Ile Lys Thr
1               5                  10                  15

Ile Val Thr Arg
            20
```

COMBINATION THERAPY FOR THE TREATMENT OF DIABETES AND OBESITY

This application claims the benefit of U.S. Provisional Application Ser. No. 60/029,233 filed Oct. 31, 1996.

FIELD OF THE INVENTION

The present invention provides a combination useful in the treatment of obesity and diabetes, either as compounds, pharmaceutically acceptable salts or pharmaceutical composition ingredients. Methods of treating obesity and diabetes are also disclosed. More particularly, the combination of the present invention comprises a metabolic rate modifying agent and a feeding behavior modifying agent; and the pharmaceutically acceptable salts and esters thereof.

BACKGROUND OF THE INVENTION

Obesity, which can be defined as a body weight more than 20% above the ideal body weight, is a major health concern in Western societies, since it is accompanied by numerous complications such as hypertension, non-insulin dependent diabetes mellitus and arteriosclerosis, which in turn cause heart disease, stroke and premature death. Obesity is the result of a positive energy balance, as a consequence of increased ratio of caloric intake to energy expenditure. The molecular factors regulating food intake and body weight balance are incompletely understood. [B. Staels et al., *J. Biol. Chem.* 270(27), 15958 (1995); F. Lonnquist et al., *Nature Medicine* 1(9), 950 (1995)]. Although the genetic and/or environmental factors leading to obesity are poorly understood, several genetic factors have recently been identified.

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor-mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

Recently, assays have been developed which more accurately predict the effects that can be expected in humans. These assays utilize cloned human $\beta_3$ receptors which have been expressed in Chinese hamster ovary cells. See Emorine et al, *Science*, 1989, 245:1118–1121; and Liggett, *Mol. Pharmacol.*, 1992, 42:634–637. The agonist and antagonist effects of the various compounds on the cultivated cells provide an indication of the antiobesity and antidiabetic effects of the compounds in humans.

These developments have recently led to the discovery of potent and selective $\beta_3$ agonists useful for treating obesity and diabetes. For example, U.S. Pat. No. 5,451,677, issued Sep. 19, 1995, hereby incorporated by reference, describes substituted phenyl sulfonamides which are selective $\beta_3$ agonists useful for treating obesity and diabetes. These phenyl sulfonamide compounds have been found to be useful in the composition and methods of the instant invention.

More recently, a potent and selective $\beta_3$ agonist, (R)-N-[4-[2-[[2-Hydroxy-2-(pyridin-3-yl)ethyl]amino]ethyl]-phenyl]-4-[4-(3-cyclopentylpropyl)-5-tetrazolon-1-yl]benzenesulfonamide, hereinafter referred to as Compound A, has been identified.

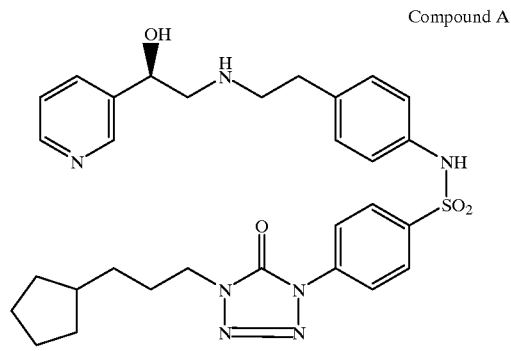

Compound A

The synthesis of Compound A and its utility for treating obesity and diabetes is described in detail in PCT International application publication number WO 95/29159, published Nov. 2, 1995, and in U.S. Pat. No. 5,561,142, issued Oct. 1, 1996. Thus, $\beta_3$ agonists, such as Compound A, are useful agents for increasing metabolic rate in mammals.

In addition to $\beta_3$ agonists which act on obesity and diabetes by increasing metabolic rate, researchers have recently cloned the mouse OB gene and its human homologue. [Y. Zhang et al., *Nature* 372, 425 (1994)]. The OB gene product, i.e., the OB protein (also known as leptin), a 167 amino acid polypeptide, has been shown to result in a dose- and time-dependent weight loss when administered to mice via intraperitoneal (IP) injection. [M. A. Pelleymounter et al., *Science* 269, 540 (1995)]. This weight loss effect is attributable to both a reduction in food intake and an increase in energy expenditure. Moreover, since both the mouse and human OB protein have this same effect when administered to mice, the possibility exists that similar effects would also occur in humans. [J. L. Halaas et al., *Science* 269, 543 (1995)].

Neuropeptide Y (NPY), a 36 amino acid member of the pancreatic polypeptide family with widespread distribution throughout the mammalian nervous system, is another agent which has been identified as being connected with feeding behavior. Neuropeptide Y is involved in regulating eating behavior and is an extremely potent orixigenic agent [See e.g., Stanley, B. G., et al., *Peptides* 13: 581–587 (1992); Sahu, A. and S. P. Kalra, *Trends In Endocrinology And Metabolism* 4(7): 217–224 (1993)]. When administered intracerebroventricularly or injected into the hypothalamic paraventricular nucleus (PVN) it elicits eating in satiated rats [Clark, J. T., et al., *Endocrinology* 115(1): 427–429 (1984); Stanley, B. G. and S. F. Leibowitz, *Proc. Natl. Acad. Sci. USA* 82: 3940–3943 (1985); Stanley, B. G. and S. F. Leibowitz, *Life Sci.* 35(26): 2635–42 (1984)] and intraventricular injection of antisera to NPY decreases eating [Stanley, B. G., et al., *Peptides*, supra; Sahu, A. and S. P. Kalra, supra]. It has been shown to stimulate appetite in a variety of species and at different stages of development [Stanley, B. G., Neuropeptide Y in multiple hypothalamic sites controls eating behavior, endocrine, and autonomic systems for body energy balance, in *Neuropeptide* Y, W. F. Colmers and C. Wahlestedt, Editor. 1993, Humana Press: Totowa, N.J. p. 457–509.]

NPY elicits a broad range of physiologic effects through activation of at least five receptor subtypes known as Y1 [WO 93/09227, published May 13, 1993], Y2 [U.S. Pat. No. 5,545,549, issued Aug. 13, 1996; WO 95/21245, published Aug. 10, 1995], Y3, Y4 [U.S. Pat. No. 5,516,653, issued May 14, 1996; WO 95/17906, published Jul. 6, 1995] and the "atypical Y1," also known as Y5. Although it has recently been reported that the Y5 receptor is the key subtype responsible for the feeding behavior response in mammals [WO 96/16542, published Jun. 6, 1996], it has now been found that the other subtypes (e.g., NPY1, NPY4) may also be involved in weight control, for example by effects on metabolic rate.

The hypothalamus plays a central role in the integrated regulation of energy homeostasis and body weight, and a number of hypothalamic neuropeptides, for example NPY, galanin, corticotrophin releasing factor (CRF), have been implicated in the mediation of these effects. Additionally, when melanin-concentrating hormone (MCH) was injected into the lateral ventricles of rats, their food consumption increased suggesting that MCH participates in the hypothalamic regulation of feeding behavior; this increase in food consumption was similar to that seen after galanin administration and somewhat less than seen after NPY treatment. [D. Qu et al., *Nature* 380: 243–247 (1996)]. Similarly, intracerebroventricular (ICV) glucagon-like peptide 1 (GLP-1) powerfully inhibited feeding in fasted rats suggesting that central GLP-1 is yet another hypothalamic physiological mediator of satiety. [M. D. Turton et al., *Nature* 379: 69–72 (1996)].

Other mechanisms and agents which have been implicated as playing a role in the regulation of feeding behavior include serotonin reuptake inhibitors such as dexfenfluramine, urocortin agonists, CCK agonists, 5-HT$_{2A}$ agonists and 5-HT$_{2C}$ serotonin receptors. It has been shown that mice lacking 5-HT$_{2C}$ serotonin receptors are overweight as a result of abnormal control of feeding behavior, thereby establishing a role for this receptor in the serotonergic control of appetite. [L. H. Tecott et al., *Nature* 374: 542–546 (1995)]. A 5-HT$_{2C}$ agonists would therefore be useful for inhibiting food intake. Indeed, a metabolite of dexfenfluramine, (+)norfenfluramine is an agonist at 5-HT2C receptors [M. Spedding et al., *Nature* 380: 488 (1996)]

It is an object of the present invention to identify compositions useful for the treatment of obesity and/or diabetes. It is a further object of the invention to identify methods of treating obesity or diabetes.

It has now been found that a combination of a metabolic rate modifying agent and an agent which modifies feeding behavior, for example, by reducing total food intake or by reducing caloric intake or selectively reducing intake of specific components of the diet such as carbohydrates or fats, provides effective therapy for treating obesity and diabetes. More specifically, a combination of a β$_3$ agonist and a NPY5 antagonist is particularly preferred for the treatment of obesity and diabetes.

SUMMARY OF THE INVENTION

The present invention provides a composition comprising a metabolic rate modifying agent and a feeding behavior modifying agent; and the pharmaceutically acceptable salts and esters thereof; provided that when the metabolic rate modifying agent is a β$_3$ agonist, then the feeding behavior modifying agent is not leptin, or a derivative thereof; and provided further that the metabolic rate modifying agent and the feeding behayior modifying agent are not both the same compound (i.e., the metabolic rate modifying agent and the feeding behavior modifying agent are not both: leptin, or a derivative thereof, Sibutramine or Ergoset; that is, the metabolic rate modifying agent and the feeding behavior modifying agent are two different compounds).

In one embodiment of the invention is the composition wherein the metabolic rate modifying agent is a compound which increases metabolic rate and the feeding behavior modifying agent is a compound which inhibits feeding behavior.

In a class of the invention is the composition wherein:
(a) the metabolic rate modifying agent is selected from a β$_3$ agonist, leptin, or a derivative thereof, a NPY1 antagonist, a NPY4 antagonist, a UCP1, UCP2 or UCP3 activating agent, Ergoset, a CRF agonist, an agent that inhibits the activity of a specific cAMP dependent protein kinase A (PKA) in adipocytes or a selective inhibitor of phosphodiesterase in adipocytes that would result in increased PKA mediated phosphorylation in adipocytes, or Sibutramine; and
(b) the feeding behavior modifying agent is selected from a NPY5 antagonist, leptin or a derivative thereof, a serotonin reuptake inhibitor, a MCH antagonist, a GLP-1 agonist, a 5-HT$_{2C}$ agonist, a 5-HT$_{2A}$ agonist, a galanin antagonist, a CRF agonist, a urocortin agonist, a melanocortin agonist, an enterostatin agonist, a CCK agonist, Cimetidine, a CCK secretagogue, Ergoset or Sibutramine. Preferably, the metabolic rate modifying agent is selected from a β$_3$ agonist, leptin, or a derivative thereof, a NPY1 antagonist, a NPY4 antagonist or a UCP1, UCP2 or UCP3 activating agent; and the feeding behavior modifying agent is selected from a NPY5 antagonist, leptin or a derivative thereof, a serotonin reuptake inhibitor, a MCH antagonist, a GLP-1 agonist, a 5-HT$_{2C}$ agonist, a 5-HT$_{2A}$ agonist, a galanin antagonist, a CRF agonist, a urocortin agonist, a melanocortin agonist or an enterostatin agonist.

In a subclass of the invention is the composition wherein the feeding behavior modifying agent is a NPY5 antagonist.

Illustrative of the invention is the composition wherein the metabolic rate modifying agent is selected from a β$_3$ agonist and a NPY1 antagonist. Preferably, the metabolic rate modifying agent is a β$_3$ agonist. Most preferably, the metabolic rate modifying agent is (R)-N-[4-[2-[[2-hydroxy-2-(pyridin-3-yl)ethyl]amino]ethyl]phenyl]-4-[4-(3-cyclopentylpropyl)-5-tetrazolon-1-yl]benzenesulfonamide; or a pharmaceutically acceptable salt and ester thereof.

An illustration of the invention is the composition wherein the metabolic rate modifying agent is a NPY1 antagonist.

Exemplifying the invention is the composition which comprises leptin, or a derivative thereof, and a NPY5 antagonist; and the pharmaceutically acceptable salts and esters thereof.

An example of the invention is a pharmaceutical composition comprising any of the compositions described above and a pharmaceutically acceptable carrier. Further illustrating the invention is the pharmaceutical composition made by combining a metabolic rate modifying agent, a feeding behavior modifying agent and a pharmaceutically acceptable carrier. Further exemplifying the invention is a process for making a pharmaceutical composition which comprises combining a metabolic rate modifying agent, a feeding behavior modifying agent and a pharmaceutically acceptable carrier; provided that when the metabolic rate modifying agent is a $\beta_3$ agonist, then the feeding behavior modifying agent is not leptin, or a derivative thereof; and provided further that the metabolic rate modifying agent and the feeding behavior modifying agent are not both the same compound.

More particularly illustrating the invention is a method of treating a condition selected from obesity or diabetes in a subject in need thereof which comprises administering to the subject a therapeutically effective amount of any of the compositions described above.

More specifically exemplifying the invention is a method of treating a condition selected from obesity or diabetes in a subject in need thereof which comprises administering to the subject a metabolic rate increasing agent and a feeding behavior inhibiting agent in an amount effective to treat the condition; provided that when the metabolic rate increasing agent is a $\beta_3$ agonist, then the feeding behavior inhibiting agent is not leptin, or a derivative thereof; and provided further that the metabolic rate increasing agent and the feeding behavior inhibiting agent are not both the same compound.

Another illustration of the invention is the method wherein (a) the metabolic rate increasing agent is selected from a $\beta_3$ agonist, leptin, or a derivative thereof, a NPY1 antagonist, a NPY4 antagonist or a UCP1, UCP2 or UCP3 activating agent; and (b) the feeding behavior inhibiting agent is selected from a NPY5 antagonist, leptin or a derivative thereof, a serotonin reuptake inhibitor, a MCH antagonist, a GLP-1 agonist, a $5-HT_{2C}$ agonist, a $5-HT_{2A}$ agonist, a galanin antagonist, a CRF agonist, a urocortin agonist, or a CCK antagonist, a melanocortin agonist or an enterostatin agonist.

Preferably, the feeding behavior inhibiting agent is a NPY5 antagonist and the metabolic rate increasing agent is a selected from $\beta_3$ agonist and a NPY antagonist. More preferably, the metabolic rate increasing agent is a $\beta_3$ agonist. Most preferably, the metabolic rate increasing agent is (R)-N-[4-[2-[[2-hydroxy-2-(pyridin-3-yl)ethyl]amino]ethyl]phenyl]-4-[4-(3-cyclopentylpropyl)-5-tetrazolon-1-yl]benzenesulfonamide.

Another example of the invention is the use of a metabolic rate increasing agent and a feeding behavior inhibiting agent in the preparation of a medicament for the treatment of a condition selected from obesity or diabetes which comprises an effective amount of the metabolic rate increasing agent and the feeding behavior inhibiting agent, together or separately; provided that when the metabolic rate increasing agent is a $\beta_3$ agonist, then the feeding behavior inhibiting agent is not leptin, or a derivative thereof; and provided further that the metabolic rate increasing agent and the feeding behavior inhibiting agent are not both the same compound.

More specifically illustrating the invention is a drug which is useful for treating a condition selected from obesity or diabetes, the effective ingredients of the said drug being a metabolic rate increasing agent and a feeding behavior inhibiting agent; provided that when the metabolic rate increasing agent is a $\beta_3$ agonist, then the feeding behavior inhibiting agent is not leptin, or a derivative thereof; and provided further that the metabolic rate increasing agent and the feeding behavior inhibiting agent are not both the same compound.

DETAILED DESCRIPTION OF THE INVENTION

This invention is concerned with the combination of certain compounds, or pharmaceutically acceptable salts thereof, for the treatment of obesity and diabetes. Obesity and diabetes mellitus are often treated by encouraging patients to lose weight by reducing their food intake and by increasing their metabolic rate. However, agents that reduce feed intake (e.g., leptin, leptin agonists, $5-HT_{2A}$ agonists, $5-HT_{2C}$ agonists, serotonin reuptake inhibitors, NPY5 antagonists, CCK agonists, GLP-1 agonists, galanin antagonists, glucagon agonists, MCH agonists) often do not have sustained effects on weight reduction. Thus, it has now been found that combination treatment with an agent that reduces feed intake with an agent that increases metabolic rate (e.g., $\beta_3$ selective agonist, NPY1 antagonist, leptin, leptin agonist, NPY4 antagonist) is advantageous over treatment with either agent alone in the treatment of obesity and diabetes.

As used herein, the terms "selective $\beta_3$ agonist" and "$\beta_3$ selective agonist" are synonymous and refer to agonists which are at least ten-fold selective for the $\beta_3$ adrenergic receptor subtype over the $\beta_1$ and $\beta_2$ adrenergic receptor subtypes in humans. Examples of selective $\beta_3$ adrenergic agonists which are useful in the compositions and methods of the present invention the compounds described in U.S. Pat. No. 5,541,677 and PCT International patent application Publication No. WO 95/29159, published Nov. 2, 1995, especially Compound A.

The term "selective," as used herein in reference to an agonist or antagonist of a specified receptor subtype, refers to an agonist or antagonist which binds to the specified receptor subtype with at least ten-fold greater affinity than it binds to other subtypes of the receptor.

The term "subject," as used herein refers to an animal, preferably a mammal, most preferably a human, who has been the object of treatment, observation or experiment.

The term "therapeutically effective amount" as used herein means that amount of active compound(s) or pharmaceutical agent(s) that elicits the biological or medicinal response in a tissue, system, animal or human that is being sought by a researcher, veterinarian, medical doctor or other clinician, which includes alleviation of the symptoms of the disease being treated.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes).

As used herein, the term "composition" is intended to encompass a product comprising the specified ingredients in the specified amounts, as well as any product which results, directly or indirectly, from combination of the specified ingredients in the specified amounts.

The term "CCK agonist," as used herein refers to a natural or human made compound that binds to the CCK receptor and acts as an agonist. Examples of CCK agonists useful in the compositions and methods of the present invention include, but are not limited to, the compounds disclosed in C. J. Aquino et al., *J. Med. Chem.* 1996, 39, 562–569. Moreover, utilizing the in vitro assay described by Aquino et al., one of ordinary skill in the art could readily identify CCK agonists useful in the present invention.

The term "CCK secretagogue," as used herein refers to a natural or human made compound that causes increased CCK secretion and therefore liberates more endogenous CCK to interact with the CCK receptor.

Compounds which reduce food intake include the Ob protein (i.e., leptin), as well as leptin agonists. As used herein, the terms "Ob protein," "OB protein" and "ob protein" all refer to the same protein and are also synonymous with the protein referred to as "leptin." The preparation of the mouse Ob protein is described in Examples 1–2 which follow; human Ob protein can be similarly prepared by one of ordinary skill in the art.

The combination of the present invention is defined as follows:

A metabolic rate modifying agent and a feeding behavior modifying agent. Preferably, the combination comprises a metabolic rate increasing agent and a feeding behavior inhibiting agent. Most preferably, the combination comprises a selective $\beta_3$ agonist and an NPY Y5 antagonist.

Metabolic rate modifying agents are compounds which, when administered to a subject, act to change the metabolic rate of the subject. Preferably, the metabolic rate modifying agent is a compound which increases metabolic rate when administered to the subject. Metabolic rate modifying agents especially suitable for use in the present invention are those agents which increase metabolic rate by at least 5%, preferably 10%, most preferably 20% in 24 hour energy expenditure when administered to the subject. Metabolic rate modifying agents are routinely evaluated in rodents (see, e.g., Largis, E. E., et. al., *Drug Devel. Res.* 1994, 32: 69–76; Carroll, M., et. al., *Diabetes* 1985, 34: 1198–1202), and, even when inactive in rodents, are tested in additional species such as dog and monkey before ultimately being tested in humans (see, e.g., Connacher, A. A., et. al., *Int'l J. Obesity* 1992, 16: 685–694; Connacher, A. A., et. al., *Am. J. Clin. Nutr.* 1992, 55: 258S–261S; Connacher, A. A., et. al., *Brit. Med. J.* 1988, 296: 1217–1220). One of ordinary skill in the art can readily identify compounds which are suitable for use as metabolic rate modifying agents in the compositions and methods of the present invention.

Examples of metabolic rate modifying agents include, but are not limited to, $\beta_3$ agonists, NPY1 antagonists, NPY4 antagonists, leptin, leptin agonists, and uncoupling protein ("UCP") activating agents, specifically UCP1, UCP2 and/or UCP3 activating agents. Although leptin is typically classified as an agent which inhibits food intake, leptin has other effects. For example, leptin increases metabolic rate by unknown pathways and lowers glucose and insulin in diabetic mice. Indeed, supplementing leptin with an agent that either reduces feed intake or increases metabolic rate has potential for improving the activity of leptin alone; for example, certain obese individuals have elevated endogenous leptin levels and are apparently resistant to leptin. To support this notion, it has been shown that while leptin appears to function by decreasing NPY levels in the hypothalamus it has increased activity in mice lacking the NPY gene compared to wild type mice. [Erickson et al. *Nature* 381: 415–418 (1996)]. Thus, for purposes of the present invention, leptin is useful as both a metabolic rate modifying agent as well as a feeding behavior modifying agent, provided that when the metabolic rate modifying agent is leptin than the feeding behavior modifying agent is not leptin, and vice versa (i.e., when the feeding behavior modifying agent is leptin, then the metabolic rate modifying agent is not leptin); and further provided that when the metabolic rate modifying agent is a $\beta_3$ agonists, then the feeding behavior modifying agent is not leptin.

Selective $\beta_3$ agonist compounds and their use for the treatment of obesity and diabetes are disclosed in U.S. Pat. No. 5,541,677 and PCT International patent application Publication No. WO 95/29159, published Nov. 2, 1995. Moreover, Compound A, is synthesized as shown in WO 95/29159 and as shown in Example 70 of U.S. Pat. No. 5,561,142, issued Oct. 1, 1996, hereby incorporated by reference. Compound A is (R)-N-[4-[2-[[2-Hydroxy-2-(pyridin-3-yl)ethyl]amino]-ethyl]-phenyl]-4-[4-(3-cyclopentylpropyl)-5-tetrazolon-1-yl]benzenesulfonamide, or a pharmaceutically acceptable salt thereof. Preferably, the dihydrochloride salt of Compound A is utilized in the combinations of the present invention.

The Neuropeptide Y1 receptor and methods of identifying ligands which bind to the Y1 receptor are described in WO 93/09227, published May 13, 1993. Moreover, NPY1 antagonists and their use in the diagnosis and treatment of feeding disorders are described in WO 96/14307, published May 17, 1996. The NPY1 antagonist compounds described in WO 96/14307 are preferred as metabolic rate modifying agents in the compositions and methods of the present invention. Additional NPY Y1 antagonist compounds useful as metabolic rate modifying agents are described in U.S. Pat. No. 5,554,621, EP 0 747 356 A1, EP 0747 357 A1, U.S. Pat. No. 5,552,411, WO 96/14307 and WO 96/40660. The Neuropeptide Y4 receptor and methods of identifying ligands which bind to the Y4 receptor are described in U.S. Pat. No. 5,516,653, issued May 14, 1996; and in WO 95/17960, published Jul. 6, 1995. Thus, one of ordinary skill in the art could readily identify NPY4 antagonists useful as metabolic rate modifying agents in the compositions and methods of the present invention.

Other metabolic rate modifying agents include Ergoset (Ergo Science), a dopamine agonist currently in clinical studies for both obesity and diabetes, and Sibutramine (Meridia), a monoamine reuptake inhibitor in development by Knoll (BASF), which is at the pre-registration stage (Europe, U.S.) and is the next anti-obesity agent that the FDA will consider for approval. [SPECTRUM Therapy Markets and Emerging Technologies Decision Resources Inc., Anti-Obesity Market, Press Date: Jul. 26, 1996, pages 103-1 to 103-20]. In addition, a selective CRF agonist [M. Egawa et al. *Neuroscience* 34: 771–775 (1990)], an agent that inhibits the activity of a specific cAMP dependent protein kinase A (PKA) in adipocytes or a selective inhibitor of phosphodiesterase in adipocytes that would result in increased PKA mediated phosphorylation in adipocytes are also useful in the combinations of the present invention as the metabolic rate modifying agent. Additionally, Uncoupling proteins ("UCP"), particularly UCP1, UCP2 and UCP3, have recently been identified as important mediators of thermogenesis [see, Vidal-Puig, A. et al, *Biochem. Biophys. Res. Commun.* 1997, 235(1): 79–82; Boss, O. et al., *FEBS Lett.* 1997, 408(1): 39–42; Gimeno, R. E. et al., *Diabetes* 1997, 46(5): 900–6; Fleury, C. et al, *Nat. Genet.* 1997, 15(3): 269–72; Zhou, Y. T. et al., *Proc. Natl. Acad. Sci. USA* 1997, 94(12): 6386–90]. Thus, UCP activating agents, specifically UCP1, UCP2 or UCP3 activating agents are useful as metabolic rate modifying agents in the instant invention. The utility of such metabolic rate modifying agents is supported by experiments with mice in which the RII-beta gene has been deleted that were shown to be resistant to diet induced obesity. [D. E. Cummings et al. *Nature* 382: 622–626 (1996)].

Feeding behavior modifying agents are compounds which, when administered to a subject, act to change the feeding behavior of the subject. Preferably, the feeding behavior modifying agent is a compound which inhibits feeding behavior and/or reduces food intake when administered to the subject. One of ordinary skill in the art can readily identify feeding behavior modifying agents useful in the compositions and methods of the present invention. For example, compounds which inhibit feeding behavior can be evaluated in rodents according to the procedures described in: Pelleymounter, M. A., et. al., *Science* 1995, 269: 540–543; Halaas, J. L., et. al., *Science* 1995, 269: 543–546; DeVos, P., et. al., *J. Biol. Chem.* 1995, 270: 15958–15961. Examples of feeding behavior modifying agents useful in the present invention include, but are not limited to, leptin, or derivatives thereof, leptin agonists 5-HT$_{2A}$ agonists, 5-HT$_{2C}$ agonists, serotonin reuptake inhibitors (e.g., dexfenfluramine marketed under the brand name Redux by Servier/ Interneuron), NPY5 antagonists, CCK agonists (e.g., FPL-15849: Fisons, Rhone-Poulenc Rorer), GLP-1 agonists, MCH agonists, galanin antagonists, glucagon agonists, Cimetidine (Tagamet, SmithKline Beecham), Ergoset, Subutramine, urocortin agonists [see, M. Spina, et al., *Science*, 273, Sep. 13, 1996, 1561–1564], melanocortin agonists, specifically melacortin 4 receptor (MC4R) agonists or mixed MC4R/MC3R agonists [see, Huszar, D. et al., *Cell* 1997, 88: 131–141; Fan, W. et al., *Nature* 1996, 385: 165–168] and enterostatin agonists [see, York, D. A. & Lin, L, Enterostatin: A Peptide Regulator of Fat Ingestion, in Molecular & Genetic Aspects of Obesity, 281–297 (G. A. Bray and D. H. Ryan eds., 1996) LSU Press, Baton Rouge; Lin, L. et al., *Peptides* 1997, 18(5): 657–661, describing the effect of enterostatin in chronically reducing fat intake and body weight in rats]. Preferably the feeding behavior modifying agent is selected from a NPY5 antagonist or leptin, or a derivative thereof.

The NPY Y5 receptor and methods of identifying ligands which bind to the Y5 receptor are described in detail in WO 96/16542, published Jun, 6, 1996. One of ordinary skill in the art, following the teaching of WO 96/16542, could readily identify NPY5 antagonist compounds useful in the compositions and methods of the present invention. NPY Y5 antagonists and their use in the diagnosis and treatment of feeding disorders are described in WO 97/19682, WO 97/20820, WO 97/20821, WO 97/20822 and WO 97/20823; these NPY Y5 antagonsists are particularly preferred as metabolic rate modifying agents in the compositions and methods of the present invention.

The Ob protein is obtained by expression of the recently discovered Ob gene. Expression of mouse Ob gene product in Drosophila Schneider 2 (S2) cells is described in Example 13, below. Based on the published sequence of the human Ob cDNA [Y. Zhang et al., *Nature* 372, 425–432 (1994); R. V. Considine et al., *J. Clin. Invest.* 95, 2986–2988 (1995)], one of ordinary skill in the art could isolate human cDNA and obtain human Ob protein by expression of the human Ob cDNA in Drosophila S2 cells according to the protocol of Example 1. Similarly, the Ob protein may also be expressed in a bacterial expression system such as *E. coli* or a yeast system and purified by one of ordinary skill in the art.

In addition to the Ob protein, compounds which cause increased expression of the Ob protein (for example, glucocorticoids, see P. De Vos, *J. Biol. Chem.* 270(27), 15958–15961 (1995)) are also useful in combination and methods of the present invention for treating obesity and diabetes. Further included within the invention are derivatives of Ob protein in which the protein is truncated to produce a small peptide and/or one or more amino acids are deleted, added, substituted or modified but which derivatives maintain the biological effect on feeding behavior and food intake and/or metabolic rate. Examples of leptin derivatives (e.g., truncated forms of leptin) which are useful in the present invention include U.S. Pat. Nos. 5,552,524; 5,552, 523; 5,552,522; 5,521,283; and PCT International application publication nos. WO 96/23513; WO 96/23514; WO 96/23515; WO 96/23516; WO 96/23517; WO 96/23518; WO 96/23519; WO 96/23520, all published on Aug. 8, 1996.

The pharmaceutically acceptable salts of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quatemized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The pharmaceutically acceptable salts of the composition of the instant invention include the composition wherein one of the individual components of the combination is in the form of a pharmaceutically acceptable salt, or the composition wherein all of the individual components are in the form of pharmaceutically acceptable salts (wherein the salts for each of the components can be the same or different), or a pharmaceutically acceptable salt of the combined components (i.e., a salt of the composition). In one embodiment of the present invention, the hydrochloride salt of the composition is utilized.

The pharmaceutically acceptable esters in the present invention refer to non-toxic esters, preferably the alkyl esters such as methyl, ethyl, propyl, isopropyl, butyl, isobutyl or pentyl esters, of which the methyl ester is preferred. However, other esters such as phenyl-C$_{1-5}$ alkyl may be employed if desired.

Esterification of alcohols, such as Compound A of the present invention, is performed by a variety of conventional procedures, including reacting the alcohol group with the appropriate anhydride, carboxylic acid or acid chloride. These reactions, as well as other methods of esterification of alcohols, are readily apparent to the skilled artisan.

Reaction of the alcohol with the appropriate anhydride is carried out in the presence of an acylation catalyst, such as 4-DMAP (4-dimethylaminopyridine, also known as N,N-dimethylaminopyridine), pyridine, or 1,8-bis [dimethylamino]napthalene.

Reaction of the alcohol with the appropriate carboxylic acid is carried out in the presence of a dehydrating agent and, optionally, an acylation catalyst. The dehydrating agent, which serves to drive the reaction by the removal of water is selected from dicyclohexylcarbodiimide (DCC), 1-[3-dimethylarninopropyl]-3-ethylcarbodiimide (EDC) or other water soluble dehydrating agents.

Alternatively, reaction of the alcohol with appropriate carboxylic acid can also result in esterification, if performed instead in the presence of trifluoroacetic anhydride, and, optionally, pyridine. A further variant is reacting the alcohol with appropriate carboxylic acid in the presence of N,N-carbonyldiimidazole with pyridine.

Reaction of the alcohol with the acid chloride is carried out with an acylation catalyst, such as 4-DMAP or pyridine.

During any of the above methods for forming esters, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

In one aspect, the present invention provides a combination of compounds or a pharmaceutically acceptable ester thereof: or a pharmaceutically acceptable salt thereof for use in the treatment of obesity in human or non-human animals.

The present invention further provides a combination of compounds, or a pharmaceutically acceptable ester thereof; or pharmaceutically acceptable salt thereof, for use in the treatment of hyperglycemia (diabetes) in human or non-human animals.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The combination of the present invention is useful for treating both Type I and Type II diabetes. The combination is especially effective for treating Type II diabetes.

The combination of compounds of the present invention is useful in the treatment of obesity and diabetes. For these purposes, the combinations of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically acceptable carriers, adjuvants and vehicles.

Thus, in accordance with the combination of the present invention there is further provided a method of treating and a pharmaceutical composition for treating obesity and diabetes. The treatment involves administering to a patient in need of such treatment a pharmaceutical composition comprising a pharmaceutical carrier and a therapeutically effective amount of each compound in the combination of the present invention.

These pharmaceutical compositions may be in the form of orally-administrable suspensions or tablets; nasal sprays; sterile injectable preparations, for example, as sterile injectable aqueous or oleaginous suspensions or suppositories.

In accordance with the methods of the present invention, the individual components of the combination can be administered separately at different times during the course of therapy or concurrently in divided or single combination forms. For example, in a two-component combination which is the $\beta_3$ agonist, Compound A, and a NPY5 antagonist, treatment with the NPY5 antagonist can commence prior to, subsequent to or concurrent with commencement of treatment with Compound A. Furthermore, the term administering also encompasses the use of prodrugs of the $\beta_3$ agonist and/or NPY5 antagonist which convert in vivo to a selective $\beta_3$ agonist or NPY5 antagonist. The instant invention is therefore to be understood as embracing all such regimes of simultaneous or alternating treatment and the term "administering" is to be interpreted accordingly.

When any of the active ingredients (e.g. Compound A) are administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds utilized in the combination may also be administered in intravenous (both bolus and infusion), intraperitoneal, subcutaneous, topical with or without occlusion, or intramuscular form, all using forms well known to those of ordinary skill in the pharmaceutical arts. When administered by injection, the injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The active ingredients of the combination (e.g., Compound A) of the present invention may be administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of the active ingredients. The percentage of active ingredients in these compositions may, of course, be varied and may conveniently be between about 2 percent to about 60 percent of the weight of the unit. The amount of active ingredients in such therapeutically useful compositions is such that an effective dosage will be obtained. The active compounds can also be administered intranasally as, for example, liquid drops or spray.

The effective dosage of each of the active ingredients employed in the combination may vary depending on the particular compound employed, the mode of administration, the condition being treated and the severity of the condition being treated. Thus, the dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

The compounds of this invention can be administered to humans in the dosage ranges specific for each compound. In general, for treating obesity and/or diabetes, the metabolic rate modifying agent is administered at a daily dosage of from about 0.001 to about 20 mg/kg of animal body weight, preferably given in a single dose or in divided doses two to six times a day, or in sustained release form; in the case of an adult human, the total daily dose will generally be from about 0.07 milligrams to about 3500 milligrams of the metabolic rate modifying agent. In general, for treating obesity and/or diabetes, the feeding behavior modifying agent is administered at a daily dosage of from about 0.001 to about 20 mg/kg of animal body weight, preferably given in a single dose or in divided doses two to six times a day, or in sustained release form; in the case of an adult human, the total daily dose will generally be from about 0.07 milligrams to about 3500 milligrams of the feeding behavior modifying agent.

More specifically, when treating diabetes mellitus and/or hyperglycemia generally satisfactory results are obtained when Compound A, or a pharmaceutically acceptable salt thereof, is administered at a daily dosage of from about 0.001 milligram to about 20 milligram per kilogram of animal body weight, preferably given in a single dose or in divided doses two to six times a day, or in sustained release form. In the case of an adult human, the total daily dose of Compound A will generally be from about 0.07 milligrams to about 3500 milligrams. The Ob protein is administered at a daily dosage of from about 0.05 mg/kg to about 20 mg/kg, preferably injected in a single dose or in divided doses 2 to 3 times per day, or in sustained release form. Preferably, the daily dosage of Ob protein is from about 0.05 mg/kg to about 5 mg/kg. The NPY5 antagonist is administered at a daily dosage of from about 0.001 mg/kg to about 20 mg/kg, preferably given in a single dose or in divided doses two to six times a day, or in sustained release form; in the case of an adult human, the total daily dose of NPY5 antagonist will generally be from about 0.07 milligrams to about 3500 milligrams. The NPY1 antagonist is administered at a daily dosage of from about 0.001 mg/kg to about 20 mg/kg, preferably given in a single dose or in divided doses two to six times a day, or in sustained release form; in the case of an adult human, the total daily dose of NPY1 antagonist will generally be from about 0.07 milligrams to about 3500 milligrams. The dosage regimen of any of the individual components of the combination may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

When treating obesity, in conjunction with diabetes and/or hyperglycemia, or alone, generally satisfactory results are obtained when Compound A is administered at a daily dosage of from 0.01 milligram to about 20 milligrams per kilogram of animal body weight, preferably given in a single dose or in divided doses two to six times a day, or in sustained release form. In the case of an adult human, the total daily dose of Compound A will generally be from about 0.7 milligrams to about 3500 milligrams. The Ob protein is administered at a daily dosage of from about 0.05 mg/kg to about 20 mg/kg, preferably given in a single dose or in divided doses 2 to 3 times per day, or as a constant infusion. Preferably, the daily dosage of Ob protein is from about 0.05 mg/kg to about 5 mg/kg. The NPY5 antagonist is administered at a daily dosage of from about 0.001 mg/kg to about 20 mg/kg, preferably given in a single dose or in sustained release form; in the case of an adult human, the total daily dose of NPY5 antagonist will generally be from about 0.07 milligrams to about 3500 milligrams. The NPY1 antagonist is administered at a daily dosage of from about 0.001 mg/kg to about 20 mg/kg, preferably given in a single dose or in divided doses two to six times a day, or in sustained release form; in the case of an adult human, the total daily dose of NPY1 antagonist will generally be from about 0.07 milligrams to about 3500 milligrams. The dosage regimen of any of the components of the combination may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The following examples are provided so that the invention might be more fully understood. They should not be construed as limiting the invention in any way.

EXAMPLE 1

Expression of Mouse Ob Gene Product in Drosophila S2 Cells

Total white adipose RNA was isolated from Swiss-Webster mice and first strand cDNA synthesized. Using the polymerase chain reaction (PCR), the coding region of the ob cDNA was isolated as 2 overlapping fragments using the following primer sets (5' CAGTGAGCCCCAAGAAGAGG 3' (SEQ. I.D. NO: 1), 5' TCCAGGTCATTGGCTATCTG 3' (SEQ. I.D. NO: 2)) and (5' ATTCCTGGGCTTCAGGG-GATTCTGAGTTTC 3' (SEQ. I.D. NO: 3), 5' GCGTGTAC-CCACGGAGGAAC 3' (SEQ. I.D. NO: 4)). The resulting 380 bp and 626 bp fragments were purified and used as templates in a subsequent PCR reaction with primers 5' AAGAATTCATGTTGCTGGAGACCCCTGTGTC 3' (SEQ. I.D. NO: 5) and 5' AAGGATCCTCAGCAT-TCAGGGCTAACATC 3' (SEQ. I.D. NO: 6).

The final 501 bp fragment was sequenced using dyeprimer chemistry on a Perkin-Elmer/Applied Biosystems 373A sequencer. The deduced amino acid sequence encoded by this cDNA was identical to that previously described. [Y. Zhang et al., Nature 373, 425–432 (1994)]. The 501 bp fragment encoding the ob gene product was subcloned via EcoR1 and BamH1 sites into plasmid pRmHa3 [T. A. Bunch et al., Nucleic Acids Research 16, 1043–1061 (1988)]. Drosophila S2 cells were cotransfected with pUChsneo [H. Steller and V. Pirrotta, EMBO Journal 4, 167–171 (1985)] and the ob expression or control (pRmHa3) plasmid by $CaPO_4$ precipitation. A polyclonal population of transfected cells was selected with 1 mg/ml G418 and grown under serum free conditions in EXCELL 401 medium (JRH Bioscience). Cells were seeded at $2 \times 10^6$ cells/ml and $CuSO_4$ added to a final concentration of 1 mM. After 7 days, cells were removed by centrifugation and the supernatants filtered through a 0.45 µM filter. Partial purification of the ob protein:

Proteins in the supernatant were concentrated by precipitation with 50 percent $(NH_4)SO_4$. The precipitate was dissolved in Buffer A (20 mM Tris pH 8, 1 mM DTT and 1 mM EDTA) and desalted over PD-10 columns (Pharmacia) equilibrated in Buffer A. Proteins in the PD-10 eluate were subjected to Mono Q chromatography (Pharmacia) and eluted with a 0–200 mM gradient of NaCl in Buffer A. Peak fractions of ob immunoreactivity (centered at 100 mM NaCl) were identified using antiserum 103-2. Based on densitometric scanning of polyacrylamide gel containing pooled fractions eluted from the Mono Q column, the ob protein was 30 percent pure after this step. 0.5 to one milligram of this partially purified ob protein preparation was obtained per liter of S2 cells. Peak fractions were analyzed by HPLC electrospray mass spectrometry using a $C_4$ column (1×100 mm) eluted in a linear gradient of acetonitrile (zero to sixty-seven percent in 10 mM trifluoroacetic acid. This reverse phase HPLC/mass spectrometry analysis demonstrated the immunoreactive protein to have a molecular mass of 16,004 Daltons, identical to that predicted for the ob gene product after cleavage of the N terminal signal sequence between amino acids 21 and 22.

EXAMPLE 2

Immunological Methods

Antiserum 103-2 was isolated from a New Zealand white rabbit injected with a 4-branch multiple antigenic peptide corresponding to amino acids 22–41 of the mouse ob sequence, i.e., VPIQKVQDDTKTLIKTIVTR (SEQ. I.D. NO: 7). [Y. Zhang et al., Nature 372, 425–432 (1994)]. Western blot analysis was performed on nitrocellulose (BA85m 0.45 µM pore size, Schleicher and Schuell Inc.). Immunodetection of the ob gene product was performed in TBS-T (20 mM Tris-Cl pH 7.6, 137 mM NaCl, 0.1% Tween 20) utilizing the ECL kit (Amersham). The secondary antibody (anti-rabbit 1 g, horseradish peroxidase linked $F(ab')_2$ fragment, Amersham) was used at 1:3000 dilution. A single immunoreactive protein with an apparent molecular weight of 14.5 kDa was identified.

EXAMPLE 3

In Vivo Study For Combination Therapy With Compounds B and C

Compound B is defined as a molecule that inhibits feed intake such as a selective serotonin 5HT2C receptor subtype agonist, an NPY5 selective receptor antagonist, a galanin antagonist, a CCK agonist, an MCH antagonist, a CRF agonist, a urocortin agonist, a glucagon-like peptide agonist, a glucagon agonist, leptin, leptin agonist. Compound C is a compound that increases metabolic rate such as a selective beta-3 adrenergic receptor agonist (e.g., Compound A), an NPY1 receptor antagonist, leptin, leptin agonist. Human patients are given by injection (i.e., subcutaneous, intramuscular or intravenous) or orally of 0.001 to 100 mg/kg of Compound B, administered one to three times per day, together with or followed by 0.001 to 100 mg/kg Compound C, administered orally or by injection one to three times per day. The first treatment is given on day 0, and the patients are treated daily for a six month period. A set of control patients are untreated (e.g., placebo) for comparison. Body weight data are collected each week and a sustained decrease in body weight of at least 2% is observed. Statistical significance of body weight decreases is determined by performing a two-factor (group and day) analysis of variance (ANOVA) with repeated measures followed by a post hoc Least Squares Difference (LSD) test.

Determination of Plasma Insulin and Glucose Levels:

Blood is collected into heparinized capillary tubes on the day before the first treatment and daily for the first week. Thereafter, patients should individually monitor their own blood glucose daily (using commercially available kits). Blood is collected for laboratory analysis weekly at the same time that body weight measurements are taken. Blood samples are analyzed (e.g., at a registered hospital or other GLP laboratory) for glucose and insulin levels.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A composition comprising a metabolic rate modifying agent and a feeding behavior modifying agent; or the pharmaceutically acceptable salts or esters thereof; provided that when the metabolic rate modifying agent is a $\beta_3$ agonist, then the feeding behavior modifying agent is not leptin, or a derivative thereof; and provided further that the metabolic rate modifying agent and the feeding behavior modifying agent are not both the same compound.

2. The composition of claim 1, wherein the metabolic rate modifying agent is a compound which increases metabolic rate and the feeding behavior modifying agent is a compound which inhibits feeding behavior.

3. The composition of claim 2, wherein
   (a) the metabolic rate modifying agent is selected from a $\beta_3$ agonist, leptin, or a derivative thereof, a NPY1 antagonist, a NPY4 antagonist or a UCP1, UCP2 or UCP3 activating agent; and
   (b) the feeding behavior modifying agent is selected from a NPY5 antagonist, leptin, or a derivative thereof, a serotonin reuptake inhibitor, a MCH antagonist, a GLP-1 agonist, a 5-HT$_{2C}$ agonist, a 5-HT$_{2A}$ agonist, a galanin antagonist, a CRF agonist, a urocortin agonist, a melanocortin agonist or an enterostatin agonist.

4. The composition of claim 3, wherein the feeding behavior modifying agent is a NPY5 antagonist.

5. The composition of claim 4, wherein the metabolic rate modifying agent is selected from a $\beta_3$ agonist or a NPY1 antagonist.

6. The composition of claim 5, wherein the metabolic rate modifying agent is a $\beta_3$ agonist.

7. The composition of claim 6, wherein the $\beta_3$ agonist is (R)-N-[4-[2-[[2-hydroxy-2-(pyridin-3-yl)ethyl]amino]ethyl]phenyl]-4-[4-(3-cyclopentylpropyl)-5-tetrazolon-1-yl]benzenesulfonamide; or a pharmaceutically acceptable salt and ester thereof.

8. The composition of claim 5, wherein the metabolic rate modifying agent is a NPY1 antagonist.

9. The composition of claim 3, which comprises leptin, or a derivative thereof, and a NPY5 antagonist; or the pharmaceutically acceptable salts or esters thereof.

10. A pharmaceutical composition comprising the composition of claim 1 and a pharmaceutically acceptable carrier.

11. The pharmaceutical composition of claim 10, made by combining a metabolic rate modifying agent, a feeding behavior modifying agent and a pharmaceutically acceptable carrier.

12. A process for making a pharmaceutical composition which comprises combining a metabolic rate modifying agent, a feeding behavior modifying agent and a pharmaceutically acceptable carrier; provided that when the metabolic rate modifying agent is a $\beta_3$ agonist, then the feeding behavior modifying agent is not leptin, or a derivative thereof; and provided further that the metabolic rate modifying agent and the feeding behavior modifying agent are not both the same compound.

13. A method of treating obesity in a subject in need thereof which comprises administering to the subject a therapeutically effective amount of the composition of claim 2.

14. A method of treating diabetes in a subject in need thereof which comprises administering to the subject a therapeutically effective amount of the composition of claim 2.

15. A method of treating a condition selected from obesity or diabetes in a subject in need thereof which comprises administering to the subject a metabolic rate increasing agent and a feeding behavior inhibiting agent in an amount effective to treat the condition; provided that when the metabolic rate increasing agent is a $\beta_3$ agonist, then the feeding behavior inhibiting agent is not leptin, or a derivative thereof; and provided further that the metabolic rate increasing agent and the feeding behavior inhibiting agent are not both the same compound.

16. The method of claim 15, wherein
   (a) the metabolic rate increasing agent is selected from a $\beta_3$ agonist, leptin, or a derivative thereof, a NPY1 antagonist, a NPY4 antagonist or a UCP1, UCP2 or UCP3 activating agent; and
   (b) the feeding behavior inhibiting agent is selected from a NPY5 antagonist, leptin or a derivative thereof, a serotonin reuptake inhibitor, a MCH antagonist, a GLP-1 agonist, a 5-$HT_{2C}$ agonist, a 5-$HT_{2A}$ agonist, a galanin antagonist, a CRF agonist, a urocortin agonist, a melanocortin agonist or an enterostatin agonist.

17. The method of claim 16, wherein the feeding behavior inhibiting agent is a NPY5 antagonist.

18. The method of claim 17, wherein the metabolic rate increasing agent is a selected from $\beta_{13}$ agonist and a NPY antagonist.

19. The method of claim 18, wherein the metabolic rate increasing agent is a $\beta_3$ agonist.

20. The method of claim 19, wherein the metabolic rate increasing agent is (R)-N-[4-[2-[[2-hydroxy-2-(pyridin-3-yl)ethyl]amino]ethyl]phenyl]-4-[4-(3-cyclopentylpropyl)-5-tetrazolon-1-yl]benzenesulfonamide.

\* \* \* \* \*